United States Patent [19]

Obermeier

[11] Patent Number: 4,845,032

[45] Date of Patent: Jul. 4, 1989

[54] PROCESS FOR THE ISOLATION AND PURIFICATION OF ALPHA-INTERFERONS

[75] Inventor: Rainer Obermeier, Hattersheim am Main, Fed. Rep. of Germany

[73] Assignee: Hoechst Aktiengesellschaft, Frankfurt am Main, Fed. Rep. of Germany

[21] Appl. No.: 842,185

[22] Filed: Mar. 21, 1986

[30] Foreign Application Priority Data

Mar. 27, 1985 [DE] Fed. Rep. of Germany ....... 3511011

[51] Int. Cl.$^4$ .................. C12P 21/00; C12P 21/02; C07K 13/00; C07K 15/00
[52] U.S. Cl. .................. 435/68; 435/70; 435/811; 530/351; 424/85.7
[58] Field of Search ............ 435/68, 70, 184, 849, 435/811; 530/351; 935/29, 66, 73; 424/85.7

[56] References Cited

U.S. PATENT DOCUMENTS

| | | | |
|---|---|---|---|
| 4,405,601 | 9/1983 | McEntire et al. | 424/95 |
| 4,476,049 | 10/1984 | Kung | 260/112 R |
| 4,485,038 | 11/1984 | Chadha et al. | 435/811 |
| 4,569,908 | 2/1986 | Mark et al. | 435/811 |

FOREIGN PATENT DOCUMENTS 114506 8/1984 European Pat. Off. .

OTHER PUBLICATIONS

Davey, M. W. et al., (1976), J. Biol. Chem. 251, 7620–7625.
Ernest Rinderknecht et al., "Natural Human Interferon-γ Complete Amino Acid Sequence and Determination of Sites of Glycosylation", The Journal of Biological Chemistry, vol. 259, No. 11, Jun. 10, 1984, pp. 6790–6097.
Masateru Shin, Butyl-Toyopearl 650 as a New Hydrophobic Adsorbent for Water-Soluble Enzyme Proteins, Analytical Biochemistry, 138:259–261, (1984).

*Primary Examiner*—Thomas G. Wiseman
*Assistant Examiner*—Charles L. Patterson, Jr.
*Attorney, Agent, or Firm*—Finnegan, Henderson, Farabow, Garrett and Dunner

[57] ABSTRACT

The invention relates to a process for the isolation and purification of α-interferons by (a) dissolution of the interferon-containing crude product in guanidine. HCl solution and precipitation by dilution with water and/or (b) by chromatography on an HIC column under renaturing conditions.

5 Claims, No Drawings

PROCESS FOR THE ISOLATION AND PURIFICATION OF ALPHA-INTERFERONS

Interferon was discovered as long ago as 1956, by Isaacs and Lindemann, as an indirect inhibitor of intracellular virus multiplication. Since then, many different types of interferon of natural origin have been identified, and these are classified, in particular, by the different cells of origin, as follows:
60 -interferons from Leukocytes
62 -interferons from fibroblasts and
65 -interferons from Lyphocytes.
Chemically, the interferons, which are induced in the particular cells by appropriate stimuli, belong to the group of glycoproteins, and some of them are stable to acid (pH 2-3) and display their full antiviral action of $10^8$–$10^9$ IU/mg in a species-specific manner. The primary structures of some $\alpha$-, $\beta$- and $\gamma$-interferons, which are constructed of 146-166 amino acids, have been elucidated. In addition, interferons which do not occur naturally have been disclosed, either the structure of these having been shortened or the amino acid sequence having been modified, compared with natural interferons, by genetic engineering means.

The most recent work in the area of genetic engineering, in which interferon genes have been induced to undergo expression in *E. coli*, has shown that the glycosyl or polysaccharide side chains detected in some natural interferons appear to have no effect on the biological activity of the proteins. Moreover, the measured binding to nonglycosylated interferons from *E. coli* of antibodies which have been raised using the natural glycoprotein is comparable, which points to the predominant effect of the protein structure of the interferon as the antigenic determinant.

Because of their therapeutic power, the interferons are produced on a large scale in industry either by harvesting of culture media of appropriate cell cultures or, recently, by fermentation of *E. coli* strains in which an interferoncoding DNA vector has been closed by genetic engineering means. The processes generally used for the isolation and purification of the crude interferon preparations obtained (mean activity $10^3$–$10^4$ IU/mg protein) are affinity and adsorption chromatography. These make use of the special ability of interferon to bind with high specificity to immobilized hydrophobic ligands, metal ions, thiols, organic mercury compounds, polynucleotides and controlled pore glass and to antibodies. However, in spite of the variety of purification methods, the yields and purity of the interferons thus obtained remain unsatisfactory, as is shown by the uncertainty about the cause of the side effects in the clinical trials of interferons on humans.

The tendency of the interferons to undergo denaturing, in particular, results in considerable difficulties and gives rise, because of the formation of insoluble polymeric aggregates, in some cases to great losses during purification and isolation of interferon. Thus, new and effective isolation processes are necessary.

This object is achieved according to the invention by a process for the isolation of $\alpha$-interferons, generated by plasmids, from bacterial cultures which have been modified by genetic engineering, and of $\alpha$-interferons from culture supernatants from induced mammalian cells, which comprises the $\alpha$-interferon from appropriate, preferably freezedried, crude products containing denatured $\alpha$-interferon a) being dissolved, under denaturing conditions, in, preferably, highly concentrated aqueous guanidine hydrochloride solution and then, after removal of impurities, preferably by slow stepwise dilution with water enriched $\alpha$-interferon being precipitated in a sparingly soluble, oligomeric, denatured form and/or b) being applied to a HIC column (column for hydrophobic interaction chromatography) and then the adsorbed $\alpha$-interferon being eluted, under renaturing conditions, with an aqueous, preferably non-ionic, surfactant solution or an aqueous salt solution with a salt content below 0.1 M.

Process steps (a) and (b) can be carried out either entirely separately or consecutively.

When steps (a) and (b) are carried out consecutively, the process according to the invention has the advantage compared with the known processes that use is made of the properties of denatured interferon for the enrichment and purification, and it permits the renaturing to natural interferon to take place only in the final step of chromatographic purification. This means that working with natural interferon, is avoided. Working with natural interferon which is unavoidable with all other processes involves high losses because of the repeated necessity for removal of denatured interferon. On the contrary, natural interferon is only generated, in a manner inherent to the process, in the final stage of purification.

Process step (a) is preferably carried out such that appropriate raw materials containing interferon, in which the interferon is substantially in the denatured form, are dissolved, under known denaturing conditions, in 6-8 M guanidine. HCL, where appropriate with the addition of one of the customary reducing agents such as $\alpha$-mercaptoethanol, dithiothreitol or glutathione (C. Ghelix, J. Yon in Protein Folding, Academic Press, N.Y., London, ed. B. Horecker, No.O. Kaplan, J. Marmur, H.A. Scherazga, 1982, pages 254 et seq.) and impurities are precipitated stepwise by careful dilution with water. It is necessary during this that the denatured state of the interferon is maintained so that it is precipitated in a subsequent dilution step, at a content of 0.5 to 2 M guanidine . HCL, and can be isolated as denatured interferon in an enriched form.

This material, which usually contains more than 10 % interferon, can be further purified by process step (b).

For this purpose, it is preferably dissolved, under denaturing conditions, in about 6 M guanidine . HCL and, after rapid dilution with water to a content of about 1-3 M guanidine . HCL, where appropriate with the addition of one of the reducing agents described above, it is applied to a HIC column.

Suitable gels for HIC are n-butyl-TSK (butyl-$^R$Toyopearl 650 M). These gels used for HIC have the property of adsorbing interferon at high salt concentrations. Desorption is effected by reducing the salt concentrations, by use of a water gradient which contains 0.5 % $^R$Tween 20, in other words with renaturing conditions. In contradistinction to conventional HIC (Masateru Shin, Naoko Sakihama, Reiko Oshino and Hiroo Sasaki, Anal. Biochem. 138, 259-261, 1984) it has been found that the adsorption of interferon takes place even in the denatured form from guanidine . HCL, whereas the conventional conditions require nondenaturing salt solutions, such as ammonium sulfate solutions, which stabilize the native globular structure of the proteins.

USE EXAMPLE 1. 100 g of a freeze-dried cell digest of an interferon-producing *E. coli* strain are dissolved in 2 l of 8 M guanidine. HCL solution at pH 7, and the solution is clarified by centrifugation. The solution of the crude material is stirred into 6 l of water, and the resulting precipitate is allowed to sediment overnight in a cold room. The sediment is isolated by centrifugation and, while moist, again dissolved in 8 M guanidine. HCL (250 ml). On average, 125 ml portions of water are stirred into the solution in five consecutive steps, and the precipitate resulting in each step are removed by centrifugation. On further addition of 500 ml of water followed by stirring, a fine gelatinous precipitate which, according to radioimmunological measurement, contains about 80 % of the total interferon in the starting material is produced. The moist precipitate which has been removed by centrifugation is stored at $-18°$ C.

2. HI chromatograph: 0.2 of the denatured crude interferon is dissolved in 6 ml of 6 M guanidine . HCL solution, and the solution is diluted with 6 ml of water and applied to a chromatography column (2.5×30 cm) with $^R$Kraktogel-TSK-butyl-650, which is equilibrated with 3 M guanidine . HCL. The development of the chromatography is monitored at 280 nm using a continuous flow UV spectrophotometer. The column is developed with 3 N guanidine . HCL until an initial peak has eluted. It is then washed with water which contains 0.5 % $^R$Tween 20. Fractions of about 2 ml are collected. The flow rate is 1.5 ml/min. The major amount of the interferon appears after about 35 fractions. By means of ultrafiltration, the combined fractions can be concentrated to the desired interferon content and adjusted to an appropriate buffer. The α-interferon thus obtained is, according to SDS gel electrophoresis (without reducing agent), monomeric and has a specific activity of $3.7 \times 10^8$ interferon (IF) units (IFU) per mg of protein, which corresponds to a purity of about 74 % based on an external IF standard of $5 \times 10^8$ IFU/mg of protein. The protein content is measured using the Lowry method. The interferon activity is determined as biological activity via the cytopathic effect of vesicular stomatitis virus on bovine kidney cells (MDBK) and by radioimmunological methods. The figures from amino acid analysis substantially agree with the theoretical figures.

I claim:

1. A process for the isolation and purification of α-interferon, generated by plasmids, from bacterial cultures which have been modified by genetic engineering, and of α-interferons from culture supernatants from induced mammalian cells, which comprises a) dissolving α-interferon from a crude product containing denatured α-interferon, under denaturing conditions, in 6 to 8 Molar guanidine hydrochloride solution; and diluting the resulting solution with water, to a content of 0.5 to 2 Molar guanidine hydrochloride, to precipitate enriched α-interferon in a sparingly soluble, oligomeric, denatured form and b) dissolving the enriched α-interferon under denaturing conditions in 6 Molar guanidine hydrochloride solution; diluting the resulting solution with water to a content of about 3 Molar guanidine hydrochloride solution; applying the resulting product to an hydrophobic interaction chromatography column containing N-butyl TSK to adsorb α-interferon on the column; and eluting the adsorbed α-interferon under renaturing conditions with an aqueous surfactant solution or an aqueous salt solution having a salt content below 0.1 Molar.

2. The process as claimed in claim 1, wherein α-interferons from bacterial cultures which have been modified by genetic engineering are isolated and purified.

3. The process as claimed in claim 2, wherein α-interferon analoges are isolated and purified.

4. The process as claimed in claim 1, wherein the dilution with water in process step (a) is carried out stepwise.

5. The process as claimed in claim 1, wherein elution in process step (b) is carried out using an aqueous solution of a non-ionic surfactant.

* * * * *